United States Patent [19]
Martin et al.

[11] Patent Number: 5,848,893
[45] Date of Patent: Dec. 15, 1998

[54] DENTAL SPRAY SYRINGE

[76] Inventors: Daniel H. Martin; Todd E. Davis, both of 757 SE. 17th St. #383, Fort Lauderdale, Fla. 89123

[21] Appl. No.: 733,927

[22] Filed: Oct. 18, 1996

[51] Int. Cl.[6] .................................................. A61C 17/02
[52] U.S. Cl. ................................................. 433/80; 433/85
[58] Field of Search ................................. 433/80, 84, 85, 433/87, 88, 100; 604/33; 251/322

[56] References Cited

U.S. PATENT DOCUMENTS

| | | |
|---|---|---|
| 2,681,408 | 6/1954 | Bronk .......................................... 433/80 |
| 3,401,691 | 9/1968 | Beu . |
| 3,506,002 | 4/1970 | Maurer et al. ............................ 433/80 |
| 3,511,235 | 5/1970 | Stram . |
| 3,570,483 | 3/1971 | Stram .......................................... 433/80 |
| 3,640,304 | 2/1972 | Fox et al. . |
| 3,652,053 | 3/1972 | Poitras . |
| 3,874,083 | 4/1975 | Buckley . |
| 3,921,297 | 11/1975 | Vit ............................................. 433/80 |
| 4,026,025 | 5/1977 | Hunt ........................................... 433/80 |
| 4,248,589 | 2/1981 | Lewis . |
| 4,950,159 | 8/1990 | Hansen ....................................... 433/80 |
| 4,957,483 | 9/1990 | Gonser et al. . |
| 4,975,054 | 12/1990 | Esrock ....................................... 433/80 |
| 5,045,055 | 9/1991 | Gonser et al. . |
| 5,049,071 | 9/1991 | Davis et al. .............................. 433/80 |
| 5,125,835 | 6/1992 | Young . |
| 5,192,206 | 3/1993 | Davis et al. .............................. 433/80 |
| 5,199,871 | 4/1993 | Young . |
| 5,236,356 | 8/1993 | Davis et al. . |
| 5,242,300 | 9/1993 | Esrock ....................................... 433/80 |
| 5,342,195 | 8/1994 | Davis et al. .............................. 433/80 |
| 5,733,117 | 5/1998 | Coss et al. ................................ 433/85 |

*Primary Examiner*—Cary E. O'Connor

[57] ABSTRACT

A dental syringe is disclosed wherein finger actuated shutoff valves control air and water flows to a discharge nozzle. The shutoff valves are constructed with a groove into which the media inlet barb is inserted for retention. All O-rings are retained below the surface of the syringe head. The discharge nozzle is constructed with a retaining groove and retained with a snap ring.

11 Claims, 4 Drawing Sheets

DENTAL SPRAY SYRINGE

BACKGROUND OF THE INVENTION

1. Field of the Invention

In common use in the dental profession are handheld devices for discharging pressurized air and water flows into the mouth. Such devices typically include a discharge nozzle which is detachable because of the necessity to sterilize or replace it before use with a new patient.

The present invention relates partially to the retention of shutoff valve assemblies suitable for the control of air, water, or other media through a dental syringe, and operable, through a valve pushbutton, with the same hand with which the syringe is held by a user during dental procedures.

It also relates to the separation of air and water as they flow from the syringe head into the passageways in the discharge nozzle. This separation of air and water is important for dental procedures which require air, but during which no water can be present.

The present invention also relates to the retention of the discharge nozzle.

2. Discussion of the Prior Art

U.S. Pat. No. 5,045,055 relates to a dental syringe which utilizes a set screw threadedly attached to a bore in the side of the syringe head to secure the shutoff valves. Also utilized is a groove in the pushbutton into which the shutoff valve body fits when the pushbutton is depressed. The syringe head side bore and pushbutton groove are difficult to clean and introduce the possibility of contamination to the syringe, and ultimately the patient. The groove and threaded side bore also increase manufacturing costs. U.S. Pat. No. 3,874,083 also utilizes a set screw to retain the shutoff valve. U.S. Pat. Nos. 3,401,691; and 3,652,053 are other examples of devices utilizing threaded elements to secure valve components. Commonly, a tool must be supplied with which to service threaded valve components, which increases manufacturing costs.

U.S. Pat. No. 3,640,304 relies upon compressed O-rings to retain the valve assembly. U.S. Pat. No. 5,199,871 relies upon an O-ring fitted in the side of the valve passageway for valve actuator retention. The use of O-rings for this purpose provides the possibility that the valve or valve actuator could be expelled from the syringe head if the media pressure exceeded the retention ability of the O-rings. As is shown in U.S. Pat. Nos. 4,248,589 and 5,433,485; commonly a compressed O-ring at the surface of the syringe head and around the nozzle retention assembly is utilized to prevent air and water leakage. This O-ring is subject to wear when the thumbnut is loosened and then retightened with each patient. The presence of the O-ring between the syringe head and thumbnut results in a difficult-to-clean and unsightly gap.

As is shown in U.S. Pat. Nos. 3,511,235; 4,957,483; 4,248,589; and 5,236,356; commonly threaded components and a compressed collet or O-ring are utilized to secure the discharge nozzle in place in the syringe head. This sometimes makes necessary the use of a tool to remove and replace the nozzle. Also this introduces the possibility that a dentist or technician may forget to tighten the nut element after replacing the nozzle and subsequently the nozzle could be ejected under water or air pressure into the mouth of a patient.

U.S. Pat. No. 5,125,835 utilizes a finger actuated press ring as part of a nozzle retaining assembly. This press ring is pressed into the syringe head to release the nozzle. When a dentist or technician ejects a nozzle with a glove on, it is possible for the glove to become trapped between the moving press ring and stationary components, resulting in a torn glove.

U.S. Pat. No. 4,975,054 utilizes a flexible clip to retain the nozzle. This clip is deflected by the user to remove the nozzle. The position of the clip provides the possibility that the clip could be inadvertently deflected by the user, which could cause the nozzle to be ejected under water or air pressure into the mouth of a patient.

SUMMARY OF THE INVENTION

The present invention provides for a dental syringe of the type considered herein, in which the media shutoff valves are mechanically retained in place in the syringe head. The locking mechanism consists of a retaining pin extending from the media inlet hose barb and fitting into a groove provided in the wall of the shutoff valve.

The syringe head of the present invention is constructed with an O-ring bore just below the surface of the bore that houses the nozzle retention assembly. This bore allows the nozzle retention assembly to be attached flush with the surface of the syringe head. The O-ring within this bore is protected from wear and prevents media leakage. The presence of the O-ring bore wall minimizes the lateral movement of the O-ring and prevents it from being compressed beyond the range desired for a good seal.

Similarly, the syringe head is constructed with an O-ring bore just below the surface of the bore that houses the hose barb. This allows the barb to be attached flush with the surface of the syringe head. The O-ring within this bore is protected from wear and is prevented from being compressed beyond the range desired for a good seal and therefore prevents media leakage.

The present nozzle retaining assembly is threadedly secured within a syringe head bore. The assembly consists of a threaded component, and a snap ring within a groove inside said component. The nozzle is pushed through the snap ring to secure it in place. The nozzle is disengaged with a firm tug. The snap ring is calibrated to require much more pressure to disengage the nozzle than could be obtained from the regulated water or air pressure present in a dental operatory.

The advantages which are obtained through the intermediary of the present invention can be essentially ascertained in that retention of the shutoff valves is accomplished without the need for threads or a bore in the side of the syringe; the provision of few, if any, compartments where contaminants can enter; and the provision of fewer components to enable low manufacturing and assembly costs.

BRIEF DESCRIPTION OF THE DRAWINGS

Advantageous modifications and features of the invention can now be readily ascertained from the following detailed description of exemplary embodiments thereof, taken in conjunction with the accompanying drawings; in which.

DETAILED DESCRIPTION

Figure 1:
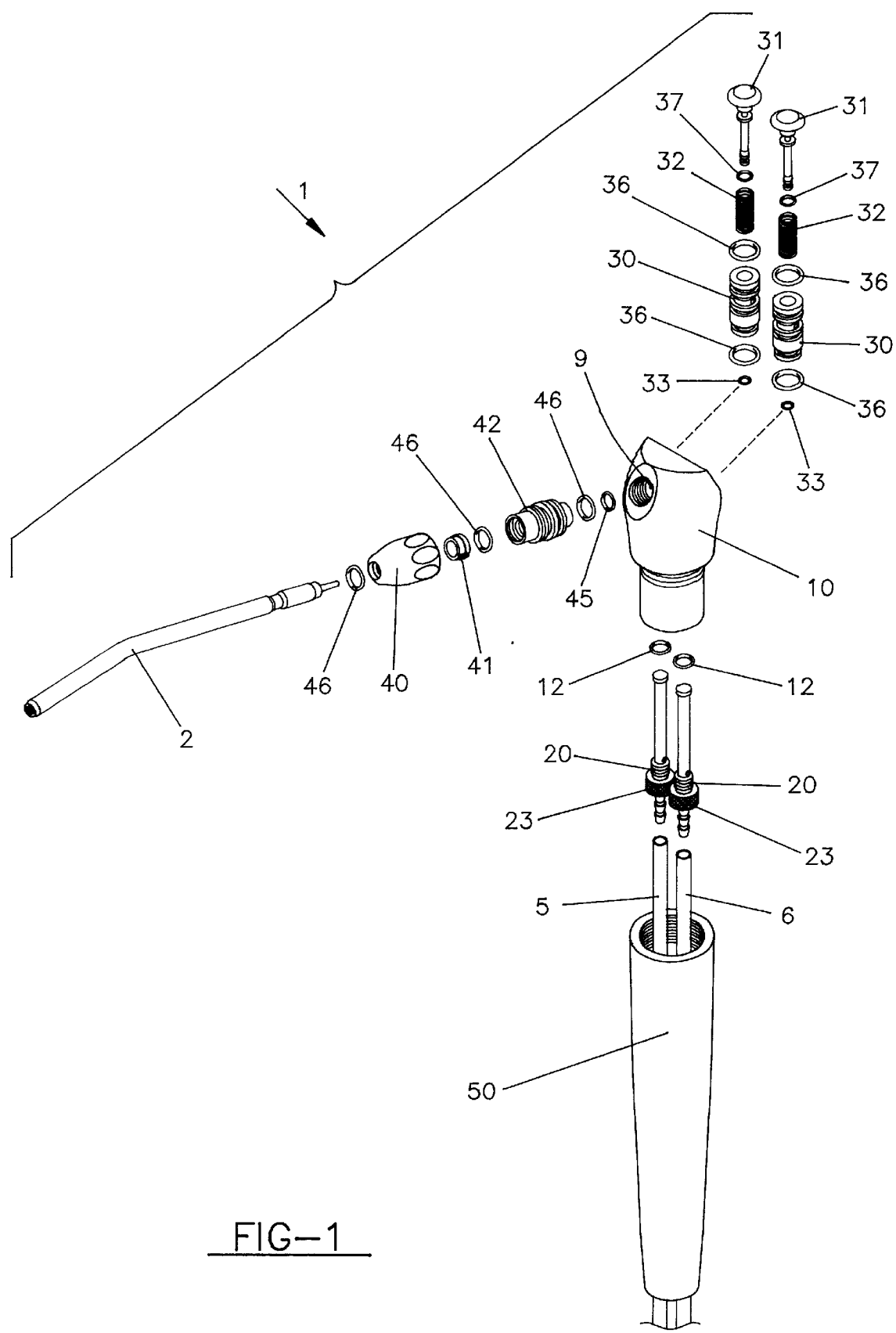
FIG. 1 is a perspective view of the inventive dental spray syringe which illustrates each component.

The illustrated dental spray syringe 1, 101 consists of a syringe head 10, 110 possessing two media connection hose barbs 20 at one end thereof covered with a projecting handle 50 and a media discharge nozzle 2, 102 at the other end.

Media connection barbs 20 with O-rings 12 are threadedly attached to the syringe head 10, 110 against sealing O-ring glands 16 by gripping onto the knurled gripping surfaces 23.

An air source 5 and a water source 6 provide air and water to media connection barb bores 21, 22, that connect to syringe head bores 3 and alongside the valve retaining pins 24 to the shutoff valve bores 7 in the syringe head.

Shutoff valves 30 are constructed with a groove 38 into which the valve retaining post 24 fits to prevent the shutoff valve from being ejected by air or water pressure.

The shutoff valves 30 are each provided with a pushbutton 31 which is depressable against the action of a return spring 32, supported by the base of the shutoff valves 30, from a closed position into an open position. Depressing the pushbuttons 31 allows media passage into the shutoff valves 30 between the pushbutton-captivated O-Rings 33, 37 into valve center bore 34, out through bore 35 and into syringe head passageways 8, 9. Sealing O-Rings 36 prevent media from escaping around the valves 30 and pushbuttons 31.

When the air pushbutton 31 is depressed, the air travels through the adapter bore 11, through adapter side bore 44, into adapter center bore 43, through nozzle side bore 49, and then is discharged from the syringe through the media discharge nozzle passageway 48. Use is made of O-rings 46 to prevent air from escaping around the tip.

When the water pushbutton 31 is depressed, the water is prevented from entering the adapter bore 11 by O-ring 45, and is discharged through the media discharge nozzle center passageway 47.

Figure 2:
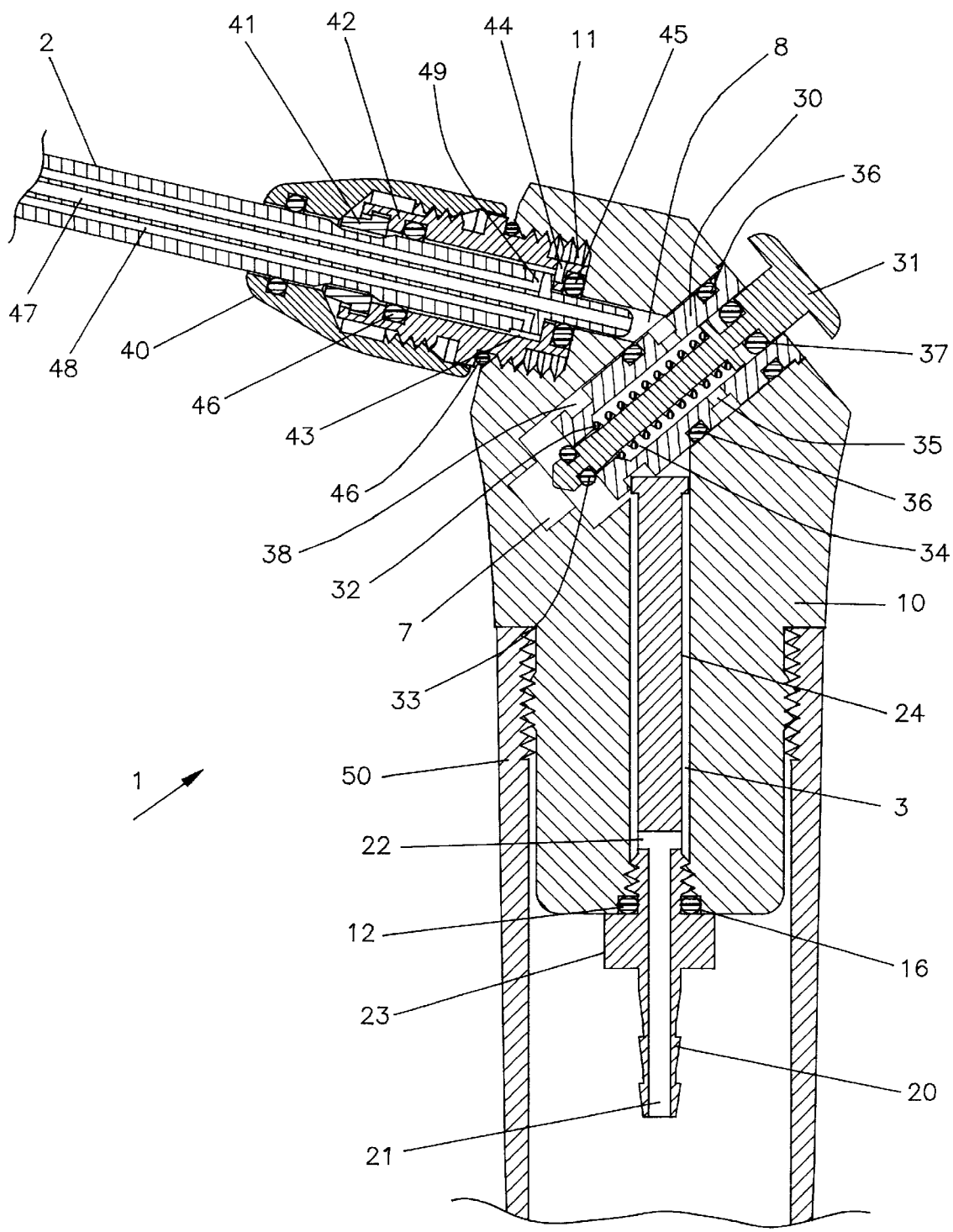
FIG. 2 illustrates on an enlarged scale a sectional view of the present invention.
Figure 3:
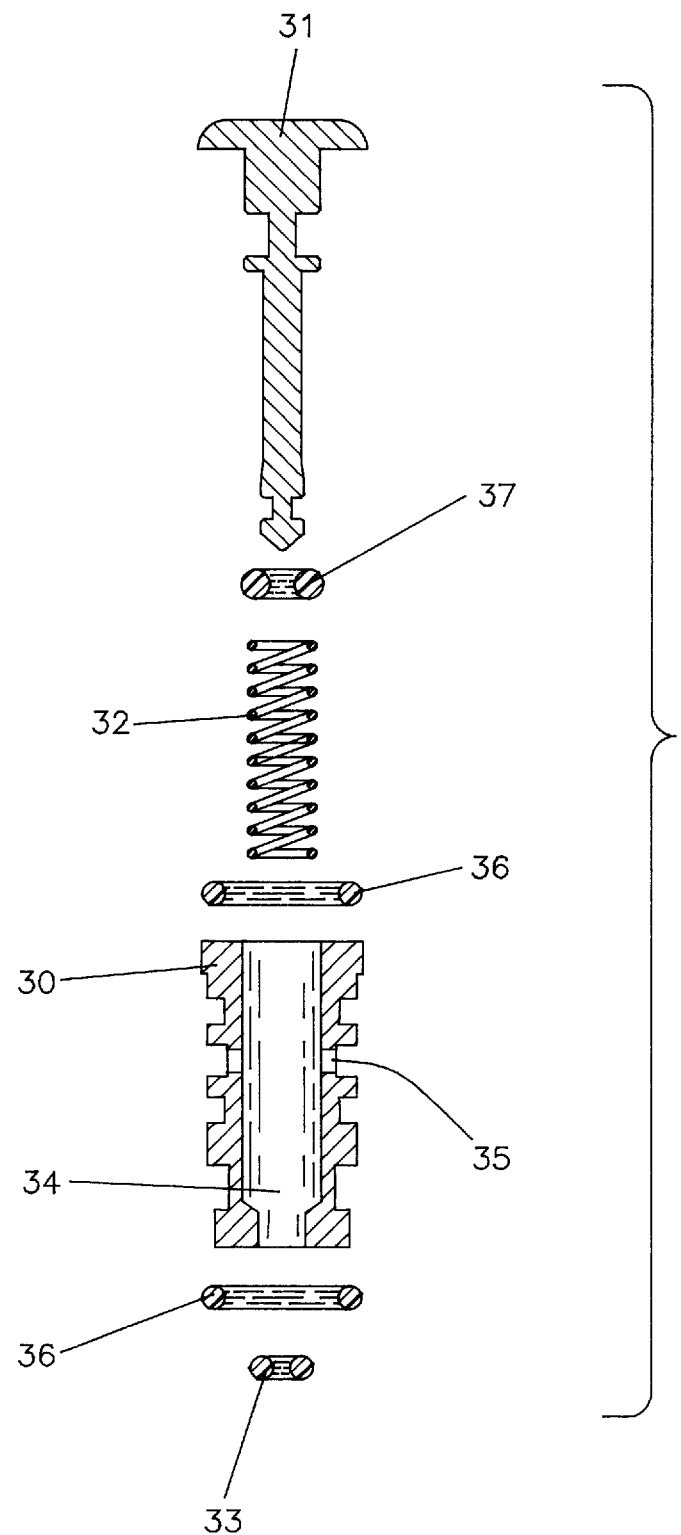
FIG. 3 illustrates on an enlarged scale a sectional view of the valve assembly of the present invention.

In the embodiment shown in FIG. 1 and FIG. 2, the nozzle 2 is retained by thumbnut 40, retaining collet 41, and adapter 42. The retaining collet 41 is captivated within the adapter 42 and is compressed by the thumbnut 40, causing it to contract on the nozzle 2 and to hold it firmly.

Figure 4:
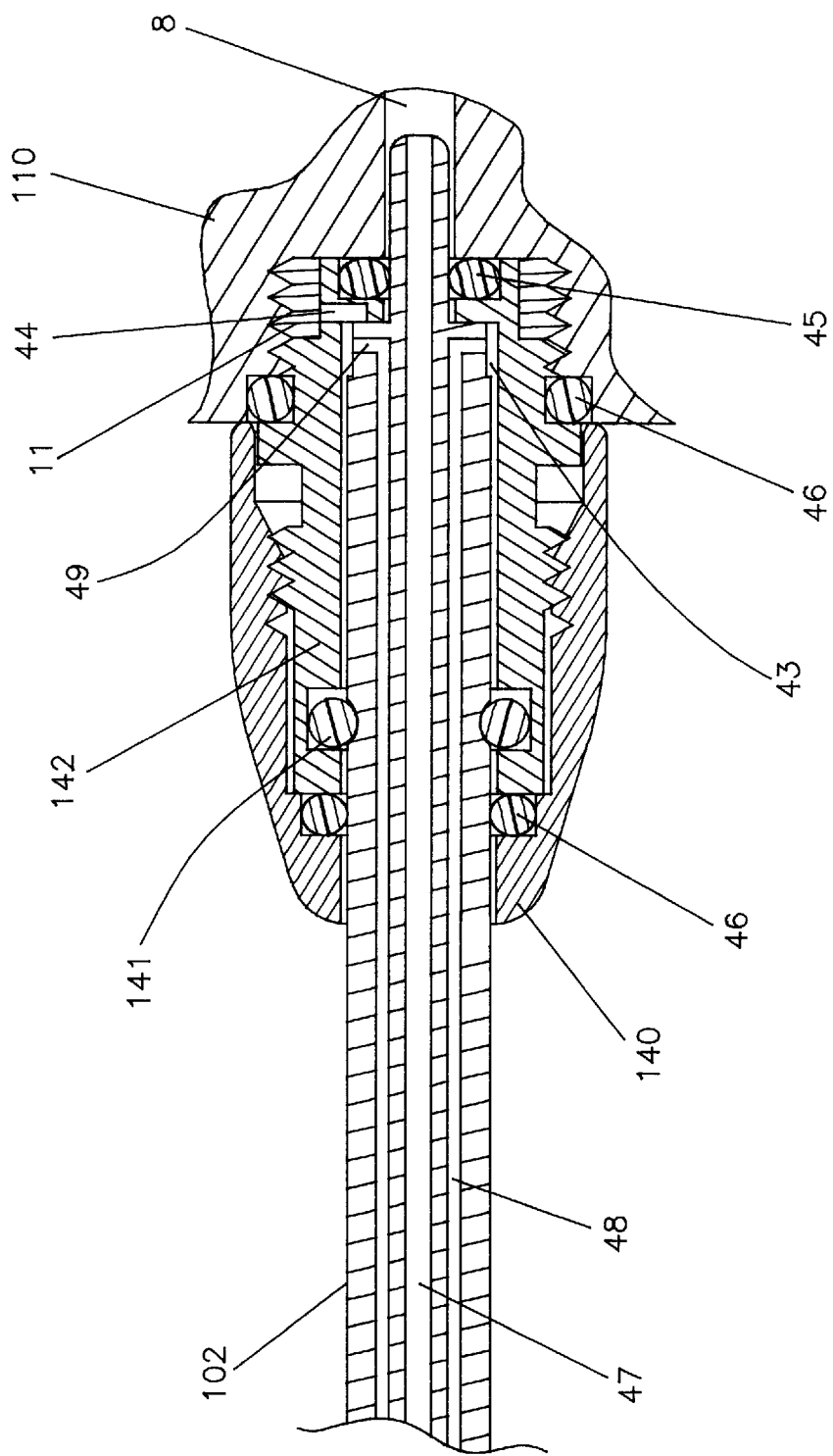
FIG. 4 illustrates on an enlarged scale a sectional view of an alternative embodiment of the nozzle raining system of the present invention.

In the embodiment shown in FIG. 4, the nozzle 102 is retained by thumbnut 140, resilient snap ring 141, and adapter 142. When the nozzle 102 is fully inserted into the adapter 142, the snap ring 141 is pressed outward, exerting pressure on the retaining groove of the nozzle 102 to hold it in place.

What is claimed is:

1. In a dental instrument assembly comprising an instrument body with at least one shutoff valve therein and a passageway constructed in said instrument body providing media flows to said valve; and valve constructed with an exterior cavity into which a retaining component within said passageway extends to fixedly hold said valve against undesired movement.

2. The dental instrument assembly of claim 1, further characterized in that said retaining component is integrally constructed with at least one annular barb.

3. The dental instrument assembly of claim 1, further comprising a threaded retention component more proximal within the instrument body passageway than the retaining component, which extends against said valve retaining component to fixedly hold said valve retaining component against undesired movement.

4. The dental instrument assembly of claim 1, further characterized in that said valve retaining component is constructed with integral threads to retain it within the instrument body passageway.

5. The dental instrument assembly of claim 1, further characterized in that said exterior cavity forms an annular axial groove about said valve.

6. The dental instrument assembly of claim 1, wherein said retaining component is constructed with a knurled exterior surface to facilitate connection without the necessity for the use of tools.

7. The dental instrument assembly of claim 1, further comprising an annular axial groove at the proximal end of said passageway, and an annular sealing member seated within said groove to provide a seal between the instrument body and the valve retaining component.

8. In a dental instrument assembly having an instrument body with at least one media passageway, a cylindrical cavity at the distal end of said passageway; and a nozzle retention assembly attached to the cylindrical cavity; wherein the improvement comprises an annular axial groove at the distal end of the cylindrical cavity, whereby an annular sealing member seated within said annular groove provides a seal between the instrument body and the nozzle retention assembly to prevent media leakage.

9. A dental instrument assembly comprising a nozzle and a nozzle retention system comprising:
   a) a hollow nozzle retention adapter constructed with at least one interior groove;
   b) a snap ring located within said groove to exert pressure upon the nozzle whenever the nozzle is connected with said adapter; and
   c) connection means for attaching said adapter to an instrument body.

10. The dental instrument assembly of claim 3, wherein said nozzle is constructed with an exterior cavity into which said snap ring extends whenever the nozzle is properly connected with the instrument body.

11. The dental instrument assembly of claim 10, further characterized in that said exterior cavity forms an annular axial groove about said nozzle.

\* \* \* \* \*